United States Patent [19]

Mendoza et al.

[11] Patent Number: 5,654,149

[45] Date of Patent: *Aug. 5, 1997

[54] NON-RADIOACTIVE DNA SEQUENCING

[75] Inventors: Leopoldo G. Mendoza; Douglas R. Storts, both of Madison, Wis.

[73] Assignee: Promega Corporation, Madison, Wis.

[*] Notice: The term of this patent shall not extend beyond the expiration date of Pat. No. 5,523,206.

[21] Appl. No.: 472,556

[22] Filed: Jun. 7, 1995

Related U.S. Application Data

[63] Continuation of Ser. No. 217,013, Mar. 23, 1994, Pat. No. 5,523,206, which is a continuation of Ser. No. 15,867, Feb. 10, 1993, abandoned.

[51] Int. Cl.$^6$ .............................. C12Q 1/68; G01N 27/26
[52] U.S. Cl. .................. 435/6; 204/462; 204/613
[58] Field of Search ........................ 435/5, 6, 91.2; 436/95; 204/182.8

[56] References Cited

PUBLICATIONS

Beidler et al, Anal. Biochem 126(2): 374–380 (1982).
Bassom et al, Anal. Biochem 196:80–83 (1991).
Maxam et al, PNAS 74: 560–564 (1977).
Sanger et al, PNAS 74: 5463–5467 (1977).

*Primary Examiner*—Eggerton A. Campbell
*Attorney, Agent, or Firm*—DeWitt Ross & Stevens SC

[57] ABSTRACT

A new process and kit are described that combines methods for generating the nucleotide base sequence of a DNA molecule with an ultra-sensitive silver staining protocol. This new combination of technologies allows for a direct, non-instrument based visualization of electrophoretically separated sequencing fragments. This non-radioactive system includes sequencing the DNA molecule by forming a set of fragments using an enzymatic dideoxy-mediated chain termination method, electrophoretically separating the DNA fragments on a gel medium, and exposing the gel medium to ultra-sensitive silver-staining solutions for a time determined by viewing the silver stain reacted primer extension products.

25 Claims, 2 Drawing Sheets

NON-RADIOACTIVE DNA SEQUENCING

This is a continuation of application Ser. No. 08/217,013, filed Mar. 23, 1994, U.S. Pat. No. 5,523,206 which is a continuation of application Ser. No. 08/015,867, filed Feb. 10, 1993 abandoned.

FIELD OF THE INVENTION

The invention is directed to a method for determining and visualizing the nucleotide base sequence of a nucleic acid molecule. More particularly, the invention is directed to a method for determining and visualizing the nucleotide base sequence of a DNA or RNA molecule utilizing a silver-staining protocol. The invention is specifically directed to a direct, non-isotopic, in-gel detection of DNA sequencing products using an ultra-sensitive silver staining method. The invention is a two component system employing (1) nucleic acid sequencing and (2) silver staining.

CITED REFERENCES

A full bibliographic citation of the references cited in this application can be found in the section preceding the claims.

DESCRIPTION OF THE PRIOR ART

Nucleic acid is a polymer consisting of chemically-linked sequences of nucleotides, which are the primary genetic material of all cells. Nucleic acid is found in two forms: deoxyribonucleic acid (DNA) and ribonucleic acid (RNA). Both forms carry within their structure the hereditary information that determines the structure of proteins, the basic building blocks of all cells.

The genetic material of all known organisms and many viruses is DNA. RNA is the primary genetic material in most plant viruses, some animal viruses and certain bacteriophages. Additionally, RNA has a role in governing protein formation in eucaryotes and procaryotes.

The basic structure of DNA and RNA is formed from four nucleotide bases. In DNA, the nucleotide bases are adenine (A), thymine (T), cytosine (C) and guanine (G). In RNA, uracil (U) is found instead of thymine. The nucleotide bases are linked into a polynucleotide chain by a backbone consisting of alternating series of sugar and phosphate residues. It is the order or sequence of the bases in the nucleic acid that determines which gene is present and ultimately which protein will be synthesized.

Although the present invention is directed to the visualization of sequenced nucleic acids as defined above, for purposes of this disclosure the terms "deoxyribonucleic acid" or "DNA" will be used interchangeably with the term "nucleic acid."

Accurately determining nucleotide base sequences is a prerequisite to further understanding the structure and function of the proteins produced by the encoded information. One such method, DNA sequencing, involves determining the order in which the nucleotide bases are arranged within a length of DNA. Two DNA sequencing techniques, which are widely known and in current use, are the chemical degradation procedure according to Maxam and Gilbert (1977, 1980) and the enzymatic dideoxy chain termination method of Sanger et al. (1977). Reference is made to Chapter 13 of Sambrook, J. et al. (1989), which is incorporated herein by reference, for a description of DNA sequencing in general and various DNA sequencing techniques.

Several modifications to the original Sanger et al. (1977) approach are now known. These include the use of modified T7 DNA polymerase in two-step synthesis reactions as described in U.S. Pat. No. 4,994,372 to Tabor and Richardson and thermal stable DNA polymerases in two-step synthesis reactions as described in U.S. Pat. No. 5,075,216 to Brow et al. and thermal cycle DNA sequencing (Craxton, 1991), all of which are incorporated herein by reference. The two-step labeling protocol and thermal cycle protocols employing thermal stable DNA polymerases can be used to minimize problems associated with DNA template secondary structure.

The recent advent of thermal cycle sequencing methodologies has increased the number of suitable sequencing templates such as lambda and cosmid templates, polymerase chain reaction (PCR) products and direct plasmid sequencing from bacterial colonies. Because the thermal cycle methods employ heat denaturation, the requirement for alkaline denaturation and ethanol precipitation of double-stranded templates has been eliminated.

Traditional methods of DNA sequencing utilize a radio-labeled oligonucleotide primer or the direct incorporation of a radiolabeled nucleotide. Although sensitive, these methods require extended exposure times and present waste disposal problems.

Fluorescent labeled oligonucleotide primers can be used in place of radiolabeled primers for sensitive detection of DNA fragments (U.S. Pat. No. 4,855,225 to Smith, et al.). Alternatively, the DNA sequencing products may be labeled with fluorescent dideoxynucleotides (U.S. Pat. No. 5,047,519 to Prober, et al.) or by the direct incorporation of a fluorescent labeled deoxynucleotide (Voss, et al., 1992). Fluorescent sequencing approaches circumvent many of the problems associated with the use of radionucleotides, but require technically sophisticated and expensive detection instrumentation.

Chemiluminescent detection circumvents many of the problems associated with the use of expensive instrumentation. In one embodiment, chemiluminescent sequencing involves the use of a biotinylated primer for the primer extension reaction. The biotin-labeled extension products are electrophoresed on a sequencing gel, transferred to a solid support, for example, a nylon membrane, and probed with a streptavidin-alkaline phosphate conjugate. The biotin-streptavidin-alkaline phosphate complex is then detected by using a suitable alkaline phosphate substrate, for example, disodium 3-(4-methoxyspiro [1,2-dioxetane-3,2'-trycyclo [3.3.1.1$^{3,7}$]decan]-4-yl) phenyl phosphate (AMPPD) or disodium 3-(4-methoxyspiro {1,2-dioxetane-3,2'-(5'-chloro) tricyclo [3.3.1.1$^{3,7}$]decan}-4-yl) phenyl phosphate (CSPD) (Martin, et al., 1991). This method is amenable to multiplexing approaches, but requires expensive reagents and difficult gel manipulations.

SUMMARY OF THE INVENTION

It is therefore an object of the present invention to provide a rapid, inexpensive alternative to radioactive, fluorescent or chemiluminescent DNA sequencing protocols.

It is also an object of this invention to provide a system for determining the nucleotide base sequence of a DNA molecule by a silver staining protocol.

Another object of the present invention is to allow direct, non-isotopic detection of electrophoretically separated sequencing products directly in a denaturing polyacrylamide gel using a sensitive silver staining technique.

These and other objects are addressed by the present invention, which is directed to a method for determining the nucleotide base sequence of a nucleic acid molecule comprising sequencing the nucleic acid molecule by forming a set of fragments of the nucleic acid molecule and separating the formed fragments on a gel medium by electrophoresis; exposing the gel medium to silver-staining solutions for a time sufficient to react the fragments with the silver-staining solutions; and determining the sequence of the DNA molecule by viewing the silver-stain reacted fragments.

The invention is also directed to a method for determining the nucleotide base sequence of a DNA molecule comprising hybridizing a primer to a DNA template molecule to be sequenced, extending the primer with a DNA polymerase, incorporating a strand terminating nucleotide onto the extended primer under conditions to yield a distinct population of nucleotide fragments beginning on the same nucleotide position for all populations and having a variable terminus at one of the following four nucleotide bases: A, C, G and T, and separating the synthesized fragments according to their size by denaturing polyacrylamide gel electrophoresis, whereby at least a part of the nucleotide base sequence of the DNA molecule can be determined, exposing the gel medium to silver-staining solutions for a time sufficient to detect the fragments with the silver-staining solutions, and determining the sequence of the DNA molecule by viewing the silver-stain reacted fragments.

The invention is further directed to a silver staining kit for DNA sequencing, comprising a container containing a DNA polymerase, a container containing a sequencing buffer, containers containing deoxy- and dideoxynucleotide mixes, a container containing a sequencing stop solution, a container containing a fix/stop solution, a container containing silver staining reagents, a container containing developer reagents, and instructions for use.

The DNA sequencing and silver staining protocol of the present invention provides a rapid, safe and inexpensive approach to visualizing DNA sequences in gels. A main advantage of the present invention is that sequencing bands can be directly detected in the gel after silver staining with the naked eye. DNA sequences can also be viewed from a photographic duplicate of the gel, using scanning instrumentation, or video imaging.

Further, the level of sensitivity compares to classical radioactive sequencing protocols. The present invention also obviates the use of isotopes, e.g., $^{32}P$, $^{33}P$, $^{35}S$, which are necessary for the autoradiographic detection of sequencing products.

The process is also very rapid, since bands can be visualized in as little as about 90 minutes after the gel is run with minimal hands-on time, thereby permitting data collection the same day. Standard isotopic techniques sometimes require several hours to days to get the adequate exposure sensitivity using standard autoradiographic film techniques.

The present invention does not require the use of special, expensive instruments such as photomultiplier-based detectors, phosphor-imagers, or laser-based fluorescent detectors for the detection of silver stained bands.

The silver sequencing system of the present invention is readily adaptable to all known enzymatic DNA sequencing protocols. As described in succeeding pages, the silver sequencing system can be used with the enzymatic dideoxy-mediated technique of Sanger et al. (1977), as well as the modified Sanger procedures using DNA polymerases in two-step synthesis reactions (U.S. Pat. No. 4,994,372 to Tabor and Richardson and U.S. Pat. No. 5,075,216 to Brow et al.) and thermal cycle DNA sequencing, as reviewed in Craxton (1991).

The sequencing system of the present invention may be utilized for a wide variety of templates useful in generating and visualizing nucleic acid sequencing products such as single-stranded (ss) M13 and phagemid clones, and ss or double-stranded (ds) templates, e.g., PCR-amplified DNA, plasmid and large ds DNA templates such as lambda and cosmid, and GC-rich and poly (A) rich templates.

The sequencing system of the present invention may also be used with a variety of known enzymes commonly used for dideoxy-mediated DNA sequencing. Non-limiting examples of these enzymes include the Klenow fragment of *E. coli* DNA polymerase I (Klenow fragment), reverse transcriptase (RT), bacteriophage T7 DNA polymerases such as SEQUENASE™ AND SEQUENASE™ Version 2.0 (United States Biochemical Corporation, Cleveland, Ohio), thermal stable DNA polymerases isolated from *Thermus aquaticus* (Taq DNA Polymerase or AMPLITAQ™; Hoffman-La Roche, Inc., Nutley, N.J.), modified Taq DNA polymerases such as Promega's Sequencing Grade Taq DNA Polymerase (SG Taq), AMPLITAQ™ DNA polymerase, Stoffel fragment (Hoffman-La Roche, Inc.) or ΔTaq™ (U.S. Biochemical Corp., Cleveland, Ohio), *Thermus thermophilus* (Tth DNA polymerase), *Bacillus caldotenax* (Bca DNA polymerase), *Thermus flavus* (Tfl DNA polymerase), *Thermococcus litoralis* [Vent$_R$™ (exo-) DNA polymerase (New England Biolabs, Inc., Beverley, Mass.)], *Bacillus stearothermophilus* (Bst® DNA polymerase, Bio-Rad Laboratories, Inc., Hercules, Calif.), and their modifications.

Further objects, features and advantages of the invention will be apparent from the following detailed description when taken in conjunction with the accompanying drawings.

Samples 1, 2, 5 and 6 illustrate the results of 2 μg of a recombinant pGEM®-5Zf(+) plasmid containing a mouse α-1-antitrypsin cDNA insert sequenced using the sequencing protocol described in Example 1;

Samples 3 and 7 illustrate the results of 750 ng of DNA obtained from a recombinant LambdaGEM®-12 phage containing a mouse α-1-antitrypsin cDNA insert sequenced using the sequencing protocol described in Example 1; and Samples 4 and 8 illustrate the results of 22 ng (60 fmol) of a 550 base pair human B-globin PCR product sequenced using the sequencing protocol described in Example 1.

Figure 2:
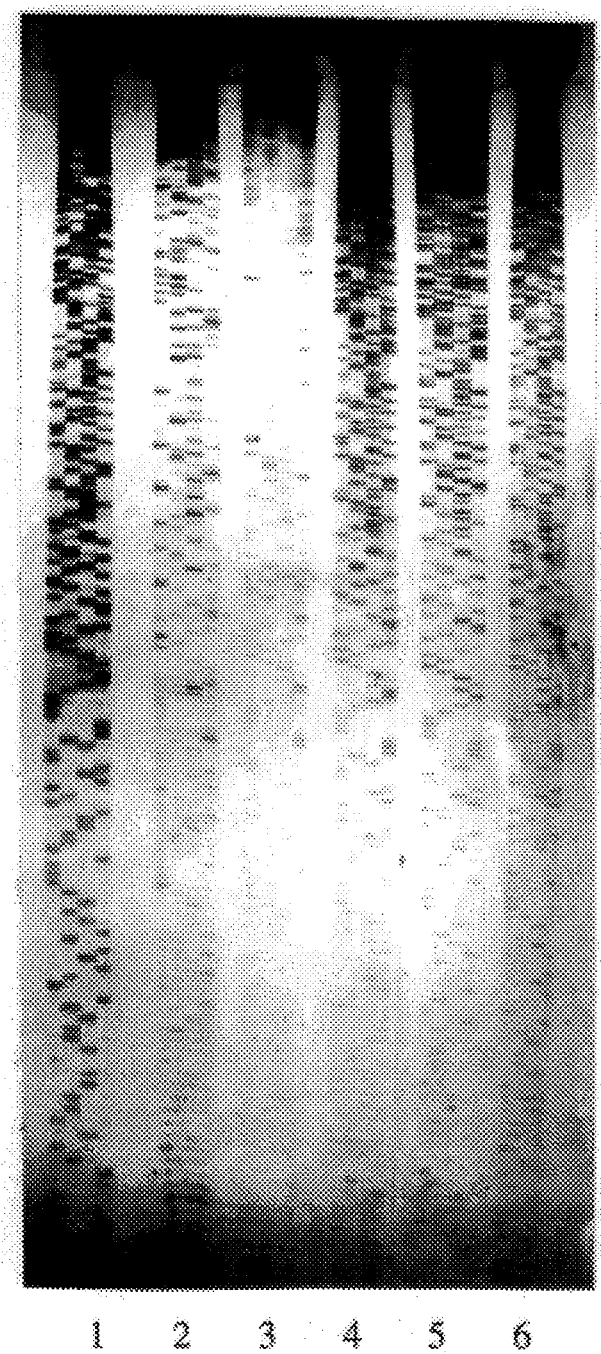

FIG. 2 is a photographic duplicate of a 6% polyacrylamide/7M urea sequencing gel containing six sequencing reactions, each of which have been subjected to the silver staining protocol according to the present invention:

Sample 1 illustrates the results of a sequencing gel run using the protocol of Example 2.

Sample 2 illustrates the results of a sequencing gel run using the New England Biolabs CIRCUMVENT™ sequencing protocol of Example 3.

Sample 3 illustrates the results of a sequencing gel run using the Perkin-Elmer Cetus AMPLITAQ™ sequencing protocol of Example 4.

Sample 4 illustrates the results of a sequencing gel run using the Promega TaqTrack™ sequencing protocol of Example 5.

Sample 5 illustrates the results of a sequencing gel run using the United States Biochemical SEQUENASE™ sequencing protocol of Example 6.

Sample 6 illustrates the results of a sequencing gel run using the BioRad Bst® sequencing protocol of Example 7.

DETAILED DESCRIPTION OF THE INVENTION

Definitions

The following definitions will be used for the present application:

The term "DNA polymerase" is used to describe an enzyme which polymerizes deoxyribonucleotides by condensing deoxynucleoside triphosphates (dNTPs) with the elimination of pyrophosphate. A nucleotide primer is essential for enzyme catalyzed polymerization.

The term "DNA Sequence" is used to describe an ordered linear array of nucleotides (polynucleotides) connected one to the other by phosphodiester bonds between the 3' and 5' carbons of adjacent pentoses.

The term "nucleotide" describes a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

The term "nucleotide base sequence" is used to describe the sequential order of a linear array of nucleotides in a DNA molecule commonly made up of four dNTPs: dATP, dCTP, dGTP and dTTP. Modified bases, other than the usual four found in DNA, such as 7-deaza-dGTP (U.S. Pat. No. 4,804, 748 to Barr, et al.) may also be incorporated.

The term "primer" describes an oligonucleotide occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primers. For example, depending on the complexity of the target sequence the oligonucleotide primer typically contains 15–25 or more nucleotides, although it may contain fewer nucleotides. Short primer molecules generally require cooler temperatures to form sufficiently stable hybrid complexes with the template.

The term "strand terminating nucleotide" is used to describe a dideoxynucleoside triphosphate (ddNTP) such as ddGTP, ddATP, ddTTP and ddCTP, which stops elongation of a DNA strand by a DNA polymerase.

The term "thermal stable enzyme" is used to describe an enzyme which is generally not irreversibly denatured by relatively high temperatures.

DNA Sequencing

The silver staining method and kit of the present invention has been developed specifically for use with a DNA sequencing system. The sequence of a DNA molecule can be determined by chemical or enzymatic methods known to the art.

The Maxam-Gilbert method involves chemical degradation of DNA strands. In this technique, end-labeled DNA molecules are modified chemically in a base-specific manner, partial strand termination is effected and the fragments thus obtained are separated by polyacrylamide gel electrophoresis. The Maxam-Gilbert method is well-known to the art. Reference is made to Sambrook et al. (1989) beginning at page 13.11 for a description of this technique.

Unlike the chemical degradation method, the dideoxymediated chain termination method (or "dideoxy method") of Sanger et al. (1977), also known as extension/termination method, starts with a DNA template and produces many DNA molecules of differing length by enzymatic extension of a synthetic primer, using DNA polymerase and a mixture of deoxy- and dideoxynucleoside triphosphates. To do this, a mixture of deoxynucleoside triphosphates and a corresponding dideoxynucleoside triphosphate is used in each of four preparations. Each preparation contains a different dideoxynucleotide. In this way statistical incorporation of the dideoxynucleotides into the growing DNA chain is achieved. After a dideoxynucleotide is incorporated into a DNA chain, it cannot grow any longer because of the absence of a 3'-OH group. Thus, many DNA fragments are formed which, from a statistical point of view, contain at least one dideoxynucleotide at every possible incorporation site and which end there. These four preparations with fragments each ending at the positions of one base are each separated in one lane on polyacrylamide gels and the sequence is usually determined after autoradiography.

An advantage of the Sanger et al. dideoxy method is that single-stranded as well as double-stranded DNA can be sequenced. The Sanger et al. method uses enzyme and chain-terminating dideoxynucleotide analogs in the enzymatic synthesis of a DNA strand. This method is preferred because it is faster and less labor intensive than sequencing by chemical means. The dideoxy method is based on the ability of a DNA polymerase to extend a primer, hybridized to the template that is to be sequenced, until a chain-terminating nucleotide is incorporated.

The procedure initiates by hybridizing a primer, preferably an oligonucleotide primer, to the DNA template to be sequenced. It is critical to have a well-defined starting nucleotide at the 5' end of the primer in the synthesis reaction. DNA polymerase extends the oligonucleotide primer until a strand-terminating dideoxynucleotide is incorporated therein. The resulting fragments, each with a common origin but ending in a different nucleotide, are then separated according to size by high-resolution denaturing gel electrophoresis.

The basis of dideoxy sequencing is the ability of base specific nucleotide analogs to terminate elongating DNA strands. Each sequence determination is generally carried out as a set of four separate reactions, each of which contains all four normal deoxynucleoside triphosphates (dNTPs) supplemented with a limiting amount of a different dideoxyribonucleoside triphosphate (ddNTP). Each population of fragments begins at the same precise 5' nucleotide position, but has a variable 3' terminus at one of the four nucleotides: A, T, C and G. Because the ddNTP lacks the necessary 3'-OH group required for chain elongation, the growing oligonucleotide is terminated selectively at one of the following nucleotide bases: G, A, T or C, depending on the respective dideoxy analog in the reaction. The relative molar concentrations of each of the dNTPs and ddNTPs can be adjusted to give a nested set of DNA strands ranging in length from a few bases to a few thousand bases. The resulting fragments, each with a common origin but ending in a different nucleotide, are separated according to size by high-resolution denaturing gel electrophoresis. See Watson, J. D., et al. (1987) and Sambrook et al. (1989), for further details on DNA sequencing in general. The separation appears on the gel as four lanes for each sample. Each lane tracks the sequence of one of the four (C, A, G, T) nucleotides. A representative illustration is found in each sample in FIGS. 1 and 2.

Sequencing Enzymes in General

Several DNA polymerases are known and commonly used for sequencing DNA: Klenow fragment, reverse transcriptase (RT), T7 DNA polymerase (SEQUENASE™ and SEQUENASE™ Version 2.0), Taq DNA polymerase, AMPLITAQ™, modified Taq DNA polymerases such as Promega's Sequencing Grade Taq DNA polymerase (SG Taq), ΔTaq™ (U.S. Biochemical Corp., Cleveland, Ohio), and AMPLITAQ™ DNA polymerase, Stoffel fragment, Vent$_R$™ (exo-) DNA polymerase, Bst™ DNA polymerase, Bca DNA polymerase, Tth DNA polymerase and Tfl DNA polymerase.

The modified T7 DNA polymerase is the preferred enzyme especially for sequencing plasmid and ss DNA templates. The enzyme is more processive than, for example, Taq DNA Polymerase or SG Taq. As a result, fewer pauses, i.e., bands at the same position in all four lanes, are observed on the sequence ladder.

Thermal stable DNA polymerases are the preferred enzymes when sequencing ds PCR amplification products, GC-rich templates and long poly (A) tails because the primer extension reactions can be performed at higher temperatures, thus alleviating some of the secondary structure associated with these templates. Large ds templates such as lambda and cosmids, and plasmids obtained directly from bacterial colonies are most efficiently sequenced with thermal stable DNA polymerases using a thermal cycle sequencing protocol. The thermal cycling results in a linear amplification of the signal strength, thereby reducing the template requirement.

Silver Staining Protocol

Once the gel has been electrophoresed, it is processed to detect the sequencing bands using the silver staining protocol. Silver staining for other non-sequencing related technologies is generally well-known to the art and, by itself, does not form a part of the invention.

Somerville and Wang (1981) and Boulikas and Hancock (1981) first described the detection of nucleic acids using a silver staining process. In 1982, Biedler, et al. suggested that silver staining may be useful for the detection of DNA bands in a sequencing gel. However, neither Biedler, et al., nor any other investigators demonstrated the use of silver staining for the visualization of DNA sequence ladders. Bassam, et al. (1991) and the corresponding International Patent Application Publication WO 92/17611 to Caetano-Anolles, et al. describe a silver staining protocol for polymerase chain reaction (PCR) amplified DNA fragments. However, neither reference describes or even suggests the detection of the bands in a DNA sequencing gel using the silver staining protocol. Further, the present invention does not employ PCR amplification techniques except to obtain the starting template material if necessary.

The gel containing the DNA sequence is sequentially immersed in volumes of solutions large enough to saturate the gel. The volume is dependent on the size of the gel. The gel is first fixed in a fixing solution, i.e., 10% acetic acid for at least approximately 30 minutes, followed by rinsing with double-distilled water (ddH$_2$O) two to three times for 2 minutes each.

Following rinsing, the gel is impregnated by the silver staining solution. A preferred silver staining solution is silver nitrate and formaldehyde (1 g/L AgNO$_3$; 0.0055% HCOH). The invention described herein preferably utilizes silver for staining the sequenced DNA fragments. It is within the scope of the present invention to use reducing metal ions other than silver. The other reducing metal ions are capable of forming in-gel complexes with nucleic acids, which can then be chemically reduced in-situ. Ionic solutions of nickel have been used to stain protein complexes (Yudelson, J. et al., 1984). Nickel and other metallic ions may be capable of staining nucleic acids. These metals may interact in a specific manner with nucleic acid components, and like silver ions may be chemically reduced in the gel to yield a visible macromolecular agglomeration of elemental metal. The general concept here is that nucleic acid sequencing fragments may be detected in denaturing polyacrylamide gels using various metal staining solutions of which silver is but one example. Various other metalic ions such as platinum, nickel, copper, or gold may be used to form complexes with nucleic acids which can be chemically reduced to stain DNA sequencing fragments in electrophoretic gels.

Following silver impregnation and a brief water rinse, about 20 seconds depending on the thickness of the gel, the gel is placed in a developer solution (30 g/L sodium carbonate, 0.0055% HCOH, 2 mg/L Na$_2$S$_2$O$_3$) until the DNA bands are observed. In order to provide better controls over the developing process, the developer can be chilled to 10°–15° C. A stop solution (10% v/v acetic acid) is then added to stop the development.

The gel may be dried using air drying or convection heating. The DNA bands may be visualized directly in the gel, by densitometry, or after photographic duplication. Other means of visualization known to the art are contemplated.

Kit

The present invention is also directed to a kit for DNA sequencing. The kit also includes reagents necessary for sequencing, the silver staining reagents, and instructions for use.

Sequencing Reagents

The reagents necessary for sequencing are selected from the group consisting of a DNA polymerase, deoxyribonucleotides, chain terminating agents, DNA sequencing primers, a reaction buffer and mixtures thereof.

Silver Stain

The localized precipitation of silver ions corresponding to the bands on the DNA ladder is created by treating with silver stain solutions. The silver stain solutions include one or more of the following: (1) a fix/stop solution; (2) silver staining reagent or solution; (3) developer reagent or solution; and/or reagents or solutions for the preparation of the gel, i.e., bonding solution (95% ethanol, 0.5% glacial acetic acid, 0.5% methacryloxypropyltrimethoxysilane) and SIGMACOTE™ (Sigma International, Ltd., St. Louis, Mo.). The silver staining solution comprises a silver salt, e.g., silver nitrate or silver perchlorate, and formaldehyde, which interact with the DNA bands to produce a dark brown-black complex upon exposure to a reducing or developer solution. The color is highly visible even to the naked eye.

DNA Sequencing Buffer

A preferred DNA sequencing buffer for the DNA sequencing is a Promega SILVER SEQUENCE™ 5× Buffer comprising 250 mM Tris-HCl (pH 9.0 at 25° C.) and 10 mM $MgCl_2$. Other buffers, known to the art, can also be used.

Deoxy/dideoxy-Nucleotide Mixes

Termination mixes contain an appropriate amount of 7-deaza-dGTP, dATP, dTTP, dCTP and the appropriate ddNTP (ddGTP for the d/ddGTP reaction, ddATP for the d/ddATP reaction, ddTTP for the d/ddTTP reaction and ddCTP for the d/ddCTP reaction). Reference is made to Example 1 for examples of termination mixes.

Sequencing Stop Solution

Sequencing stop solutions, known to the art, can be used in this process. Examples include:

95% formamide, 20 mM EDTA, 0.05% Bromophenol blue, 0.02% xylene cyanol FF;

95% formamide, 20 mM EDTA, 0.05% Bromophenol blue, 0.05% xylene cyanol FF;

95% formamide, 10 mM EDTA, 0.1% Bromophenol blue, 0.1% xylene cyanol FF;

A preferred sequencing stop solution is the Promega SILVER SEQUENCE™ stop solution comprising 10 mM NaOH; 95% formamide (v/v), 0.05% bromophenol blue (v/v); and 0.05% xylene cyanole FF (v/v). Other stop solutions, known to the art, can also be used.

Gel Fix/stop solution

The gel fix/stop solution contains between about 5% and 30% acetic acid. A preferred silver staining fix and/or stop solution is 10% v/v (glacial acetic acid). Other fix/stop solutions, known to the art, can also be used.

EXAMPLES

The following examples are intended to describe the present invention without limiting the same.

Example 1

Preferred Sequencing Protocol

Example 1 illustrates a preferred method for determining the nucleotide base sequence of a DNA molecule utilizing the silver staining method of the present invention.

Preparation of the Plasmid Template DNA

Because the thermal cycle methods employ heat denaturation, the requirement for alkaline denaturation and ethanol precipitation of double-stranded templates has been eliminated.

Sequencing Protocol

For each set of sequencing reactions, four 0.5 ml microcentrifuge tubes were labeled (G, A, T, C). Two microliters of the appropriate d/ddNTP Mix were added to each tube. The termination mixes contained 40 µM 7-deaza-dGTP, 40 µM dATP, 40 µM dTTP, 40 µM dCTP and the appropriate ddNTP (45 µM ddGTP for the d/ddGTP reaction, 525 µM ddATP for the d/ddATP reaction, 900 µM ddTTP for the d/ddTTP reaction and 300 µM ddCTP for the d/ddCTP reaction). The tubes were capped and stored on ice or at 4° C. until needed.

For each set of four sequencing reactions, the following reagents were mixed in a microcentrifuge tube: 0.02–1 pmol template DNA (see following paragraph); 5 µl 5× buffer (250 mM Tris-HCL, pH 9.0 at 25° C.; 10 mM $MgCl_2$); 4.5 pmol primer and sterile $H_2O$ to a final volume of 16 µl.

The recommended amounts of DNA template in nanograms (ng) are listed in the following table:

| Template | ng |
|---|---|
| 200 bp | 8 ng |
| (PCR product) | (0.06 pmol) |
| 3,000–5,000 bp | 2000 ng |
| (supercoiled plasmid DNA) | (1 pmol) |
| 48,000 bp | 750 ng |
| (lambda, cosmid DNA) | (0.02 pmol) |

Because supercoiled plasmid yields a weaker signal than relaxed dsDNA, a greater amount of supercoiled plasmid template, i.e., 1 pmol per reaction, is recommended. The general formula to calculate the number of micrograms of template DNA equivalent to 1 pmol is as follows:

dsDNA: 1 pmol=$(6.6 \times 10^{-4} \mu g) \times n$, where n is the number of base pairs in the template.

ssDNA: 1 pmol=$(3.3 \times 10^{-4} \mu g) \times n$, where n is the number of bases in the template.

The general formula to calculate the number of nanograms of primer equivalent to 4.5 pmol is as follows:

4.5 pmol=1.5 ng×n, where n is the number of bases in the primer.

When the reagents were mixed in the microcentrifuge tube, 1.0 µl of SG Taq (5 u/µl) was added to the primer/template mix and briefly mixed by pipetting up and down.

A 4 µl aliquot of the enzyme/primer/template mix was then added to the inside wall of each tube containing the d/ddNTP mix.

One drop (approximately 20 µl) of mineral oil was then added to each tube and briefly spun in a microcentrifuge.

The reaction tubes were placed in a thermal cycler heated to 95° C. to start the cycling program. It is important to preheat the thermal cycler to 95° C. to prevent non-specifically annealed primers from being extended (and thus stabilized) by SG Taq. Ramp times should be as rapid as possible. Cycling profiles are optimized for each primer/template combination. The following cycling profiles are used as a guideline:

Profile 1: for a primer <24 bases or with a GC-content <50%

95° C. for 2 minutes, then:
95° C. for 30 seconds (denaturation)
42° C. for 30 seconds (annealing)
70° C. for 1 minute (extension)
45–60 cycles total, then 4° C.

Profile 2: for a primer ≧24 bases or shorter primers with a GC-content ≧50%

95° C. for 2 minutes, then:
95° C. for 30 seconds (denaturation)
70° C. for 30 seconds (annealing/extension)
45–60 cycles total, then 4° C.

These programs routinely allow the sequence to be read 1–400 bases from the primer.

After completion of the thermal cycling program, 3 µl of stop solution (10 mM NaOH, 95% formamide; 0.05% bromophenal blue, 0.05% xylene cyanole) was added to the inside wall of each tube. The tubes were briefly spun in a microcentrifuge to terminate the reactions. The samples may be left overnight at 4° C. before addition of the stop solution.

The reactions were then heated at approximately 70°–95° C. for 2 minutes immediately before loading on a sequencing gel. 2.5 to 6.0 µl of each reaction was loaded on the gel. It was not necessary to remove the mineral oil overlay, as long as care is taken to draw up only the blue sample below the mineral oil when pipetting.

Preparation of the Sequencing Gel Plates

The short glass sequencing gel plate was treated with a bonding solution to chemically cross-link the gel to the glass plate according to the process of Kobayashi, Y. (1988) in order to prevent tearing of the gel during the silver staining protocol. To provide a surface for mechanical stabilization of the gel, a scrupulously clean glass plate was wiped with 1 ml of freshly prepared bonding solution (95% ethanol, 0.5% glacial acetic acid, 0.5% methacryloxypropyltrimethoxysilane). After 4 to 5 minutes, the excess bonding solution was removed by wiping the plate with 95% ethanol. Because the gel is mechanically stabilized by the glass plate, it is possible to prepare 4–5% polyacrylamide/urea gels to maximize the length of read.

The long glass sequencing gel plate was treated with a SIGMACOTE® filming medium (Sigma International Ltd., St. Louis, Mo.) to prevent the gel from adhering to the long plate. The scrupulously clean glass plate was wiped with SIGMACOTE® solution. After 5 to 10 minutes, excess SIGMACOTE® was removed by wiping the plate with a tissue.

Silver Staining the Sequencing Gel

All incubations, except the developing reaction, were performed at room temperature with constant, gentle agitation. The developer solution was prechilled to control the development reaction and minimize background staining. The listed times are suitable for standard 0.4 mm thick gels. The procedure was followed according to Bassam et al. (1991) and International Patent Application Publication WO 92/17611 to Caetano-Anolles, et al.:

(1) After electrophoresis, the glass plates were carefully separated using a plastic wedge. The gel was strongly affixed to the short glass plate.

(2) The short glass plate with the adherent gel was placed in a shallow plastic tray containing sufficient fix/stop solution (10% glacial acetic acid) to submerge the gel. The gel was agitated for at least 20 minutes. It is within the scope of the present invention to allow the gels to be stored in the fix/stop solution overnight.

(3) The gel was then rinsed three times for 2 minutes each with double-distilled water ($ddH_2O$).

(4) The gel was then soaked for 30 minutes with the staining solutions (1 g/L silver nitrate ($AgNO_3$); 0.056% formaldehyde (1.5 ml of 37% HCOH/liter)). It is within the scope of the present invention to soak the gel for longer periods of time, up to several hours.

(5) The gel was rinsed with double-distilled (dd)$H_2O$ for 20 seconds. Care should be take to maintain this rinsing step at no more than 20 seconds, as rinse times greater than 20 seconds sometimes result in significantly reduced staining intensity. Thinner gels may require a proportionately shorter water rinse.

(6) An appropriate amount of developer solution (30 g/L sodium carbonate ($Na_2CO_3$); 0.056% formaldehyde (1.5 ml of 37% HCOH/liter); 2 mg/L sodium thiosulfate pentahydrate ($Na_2S_2O_3.5H_2O$)) was prechilled to 10°–12° C. The gel was developed in the developer solution until the bands became visible, typically less than 10 minutes.

(7) To terminate the developing reaction, an equal volume of fix/stop solution was added and incubated for at least 2 to 3 minutes.

(8) The gel was then rinsed two times at 2 minutes in $ddH_2O$.

(9) The gel was allowed to dry using forced air drying, convection heating, or dried at room temperature.

Figure 1:
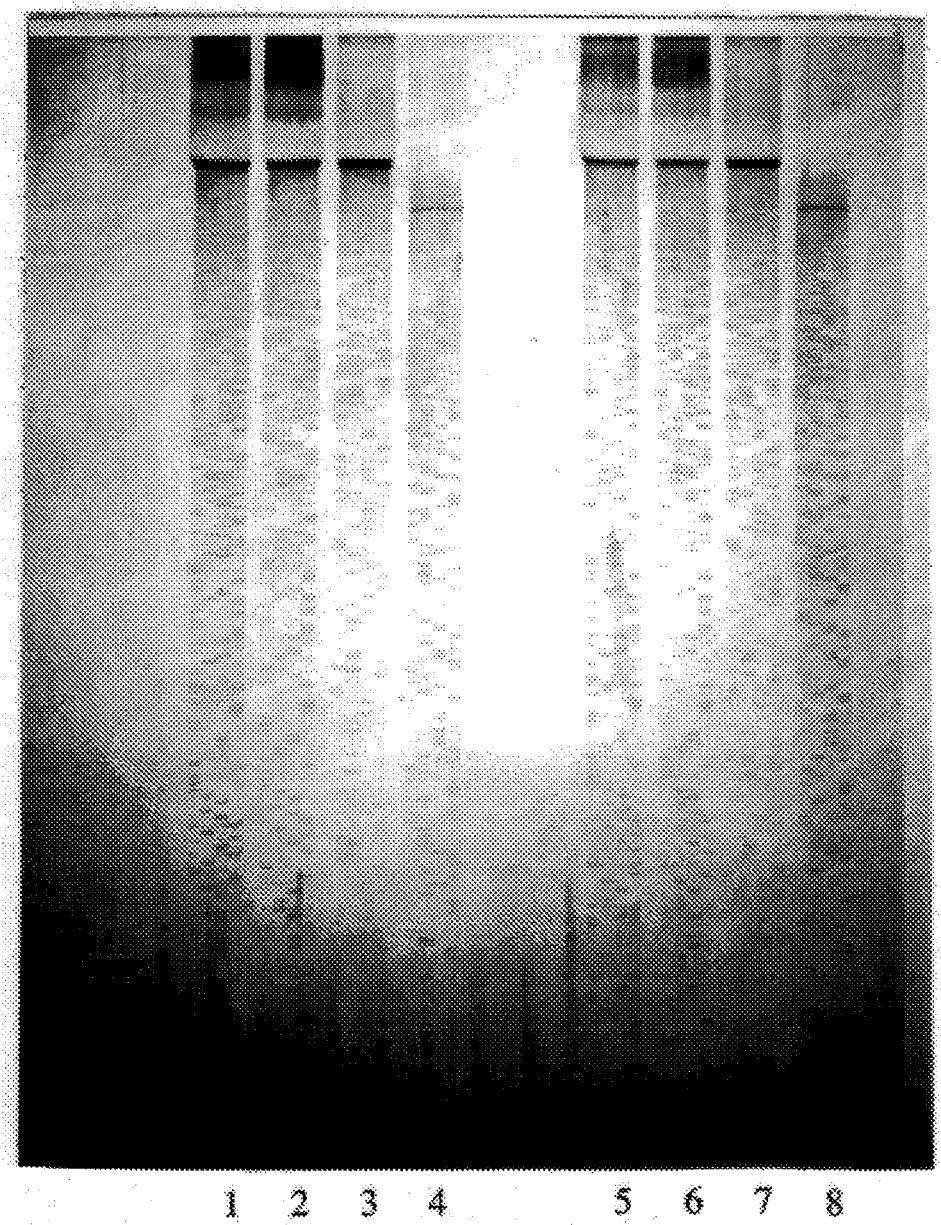
FIG. 1 is a photograph of an actual 6% polyacrylamide/7M urea sequencing gel, showing the results of the following four experiments conducted using the sequencing and staining technique of the present invention.

Reference is now made to FIG. 1, which illustrates the results of four experiments conducted using the above techniques. FIG. 1 illustrates DNA sequencing samples loaded in duplicate on a 6% polyacrylamide/7M urea sequencing gel.

Samples 1 and 5 illustrate the results of 2 µg of a recombinant pGEM®-5Zf(+) plasmid containing a mouse α-1-antitrypsin cDNA insert sequenced using the sequencing protocol described above and a pUC/M13 forward 24 mer sequencing primer. The reaction was performed for 60 cycles using cycling profile 1, except that the annealing temperature was 50° C., as opposed to 42° C.

Samples 2 and 6 illustrate the results of 2 µg of a recombinant pGEM®-5Zf(+) plasmid containing a mouse α-1-antitrypsin cDNA insert sequenced using the sequencing protocol described above and a pUC/M13 forward 24 mer sequencing primer. The reaction was performed for 60 cycles using cycling profile 2.

Samples 3 and 7 illustrate the results of 750 ng of DNA obtained from a recombinant LambdaGEM®-12 phage containing a mouse α-1-antitrypsin cDNA insert sequenced using the sequencing protocol described above and a T7 20 mer sequencing primer. The reaction was performed for 60 cycles using cycling profile 1, except that the annealing temperature was 50° C., as opposed to 42° C.

Samples 4 and 8 illustrate the results of 22 ng (60 fmol) of a 550 base pair human β-globin PCR product sequenced using the sequencing protocol described above and one of the primers (20 mer) used for the PCR amplification. The reaction was performed for 60 cycles using cycling profile 2.

Example 2

The SILVER SEQUENCE™ Sequencing Reactions

The SILVER SEQUENCE™ sequencing reactions were performed as described below. Two µg of Promega pGEM®-3Zf(+) plasmid template (not denatured) was mixed with 3.75 µl (37.5 ng; 4.7 pmol) of a pUC/M13 forward 24 mer sequencing primer, 5.0 µl of SILVER SEQUENCE™ 5× buffer (250 mM Tris-HCl, pH 9.0 at 25° C.; 10 mM $MgCl_2$) and distilled water to 15 µl. SG Taq DNA polymerase (2 µl; 10 units) was added to the mix. Aliquots (4 µl) were added to each of four 0.5 ml microcentrifuge tubes containing 2.0 µl of the appropriate termination mixes. The termination mixes contained 40 µM 7-deaza-dGTP, 40 µM dATP, 40 µM dTTP, 40 µM dCTP and the appropriate ddNTP (45 µM ddGTP for the d/ddGTP reaction, 525 µM ddATP for the d/ddATP reaction, 900 µM ddTTP for the d/ddTTP reaction and 300 µM ddCTP for the d/ddCTP reaction). The samples were overlayed with 1 drop of mineral oil and placed in a pre-heated thermal cycler (95° C.). The thermal cycle profile consisted of an initial incubation at 95° C. for 2 minutes, followed by 45 cycles of 95° C., 30 seconds and 70° C., 30 seconds. The reactions were terminated by the addition of 3 µl of SILVER SEQUENCE™ stop mix (10 mM NaOH; 95% formamide; 0.05% bromophenol blue; 0.05% xylene cyanol). The reactions were incubated at 70° C. for 2 minutes, then 6.0 µl aliquots were loaded on a 6% polyacrylamide/7M urea sequencing gel, electrophoresed and stained according to the procedure described in Example 1.

Reference is now made to Sample 1 of FIG. 2, which shows the silver-stained sequencing ladder of DNA sequenced by this protocol. FIG. 2 is a photographic duplicate of the silver-stained gel prepared with 35 cm×43 cm Electrophoresis Duplicating Film (Eastman Kodak Company, Publication KPS317a, which is incorporated herein by reference) as recommended by the manufacturer.

Example 3

The Vent$_R$™ (exo-) Sequencing Reactions

The Vent$_R$™ (exo-) sequencing reactions are known to the art and are described in New England Biolabs *CIRCUMVENT™ Thermal Cycle Dideoxy DNA Sequencing Kit Technical Manual*, which is incorporated herein by reference. Briefly, 2 µg of Promega pGEM®-3Zf(+) plasmid template (not denatured) was mixed with 3.75 µl (37.5 ng; 4.7 pmol) of a pUC/M13 forward 24 mer sequencing primer, 1.5 µl 10× CIRCUMVENT™ sequencing buffer, 1.0 µl 30× Triton X-100 and distilled water to a final volume of 12.0 µl. After the addition of 2.0 units of Vent$_R$(exo-) DNA polymerase, 3.2 µl aliquots were added to each of four 0.5 ml microcentrifuge tubes containing 3.0 µl of the appropriate termination mixes. The samples were overlayed with 1 drop of mineral oil and thermal cycled. The thermal cycle profile consisted of 25 cycles of 95° C., 20 seconds; 50° C., 20 seconds; and 72° C., 20 seconds. The reactions were terminated by the addition of 4 µl of stop mix. The reactions were incubated at 70° C. for 2 minutes, then 6.0 µl aliquots were loaded on a 6% polyacrylamide/7M urea sequencing gel electrophoresed and stained according to the procedure described in Example 1.

Reference is now made to Sample 2 of FIG. 2, which shows the silver-stained sequencing ladder of DNA sequenced by this protocol.

Example 4

The AMPLITAQ™ Sequencing Reactions

The AMPLITAQ™ sequencing reactions are known to the art and are described in the Perkin-Elmer/Cetus *AMPLITAQ™ Sequencing Kit Technical Manual*. Briefly, 4 µg of pGEM®-3Zf(+) plasmid template DNA (Promega Corp.) was alkaline denatured by the addition of 0.1 volumes of 2M NaOH. The sample was incubated for 5 minutes at room temperature, then neutralized by the addition of 0.2 volumes of 3M potassium acetate. The denatured template was ethanol precipitated by the addition of 4 volumes of ethanol, washed once with 70% ethanol, then dried. The template DNA was then resuspended in 15 µl of distilled water, 1 µl of primer (10 ng; 1.25 pmol) and 4 µl of labeling mix (contains AMPLITAQ™ DNA polymerase, buffer and nucleotides). The sample was incubated at 45° C. for 5 minutes. Aliquots (4 µl) were added to each of four tubes containing 4 µl of the appropriate termination mixes and incubated at 72° C. for 5 minutes. The reactions were terminated by the addition of 4 µl of stop mix. The reactions were incubated at 70° C. for 2 minutes, then 6.0 µl aliquots were loaded on a 6% polyacrylamide/7M urea sequencing gel, electrophoresed and stained according to the procedure described in Example 1.

Reference is now made to Sample 3 of FIG. 2, which shows the silver-stained sequencing ladder of DNA sequenced by this protocol.

Example 5

The TAQTRACK® Sequencing Reactions

The TAQTRACK® sequencing reactions are known to the art and are described in Promega's *TAQTRACK® Sequencing Systems Technical Manual*, which is incorporated herein by reference. Briefly, 4 µg of plasmid template DNA was alkaline denatured as described for the AMPLITAQ™ reaction (Example 4). The template DNA was then resuspended in 5.5 µl of distilled water, 5.0 µl of 5× reaction buffer and 2.0 µl (2.5 pmol) of primer. The sample was incubated at 37° C. for 10 minutes to facilitate primer annealing, then 1 µl (8 units) of SG Taq DNA polymerase was added to the reaction. Aliquots (6 µl) were added to each of four tubes containing 1.0 µl of the appropriate termination mixes and incubated at 70° C. for 15 minutes. The reactions were terminated by the addition of 4 µl of stop mix. The reactions were incubated at 70° C. for 2 minutes, then 6.0 µl aliquots were loaded on a 6% polyacrylamide/7M urea sequencing gel, electrophoresed and stained according to the procedure described in Example 1.

Reference is now made to Sample 4 of FIG. 2, which shows the silver-stained sequencing ladder of DNA sequenced by this protocol.

Example 6

United States Biochemical SEQUENASE™ Version 2 Sequencing Protocol

The sequencing reactions are known to the art and are described in the United States Biochemical Corp. *SEQUENASE™ Version 2.0 Technical Manual*, which is incorporated herein by reference.

Briefly, 4 µg of plasmid template DNA was alkaline denatured as described for the AMPLITAQ™ reaction (Example 4). The template DNA was then resuspended in 7 µl of distilled water, 2 µl of SEQUENASE™ reaction buffer and 1 µl of pUC/M13 forward 24 mer sequencing primer (10 ng; 1.25 pmol). The mixture was incubated at 65° C. for 2 minutes, then slowly cooled to room temperature to facilitate primer annealing. The following reagents were added to the annealed primer-template mixture: 1.0 µl 0.1M DTT, 2.0 µl of diluted labeling mix and 2.0 µl of diluted SEQUENASE™ Version 2.0. The reaction was incubated for 2 to 5 minutes at room temperature. An aliquot (3.5 µl) of the mix was then added to each of four tubes containing 2.5 µl of the appropriate termination mix. The reactions were incubated at 37° C. for 3 to 5 minutes, then terminated by the addition of 4 µl of Stop Solution. The reactions were incubated at 70° C. for 2 minutes, then 6.0 µl aliquots were loaded on a 6% polyacrylamide/7M urea sequencing gel, electrophoresed and stained according to the procedure described in Example 1.

Reference is now made to Sample 5 of FIG. 2, which shows the silver-stained sequencing ladder of DNA sequenced by this protocol.

Example 7

The Bst® Sequencing Reactions

The Bst® sequencing reactions are known to the art and are described in BioRad's *Bst® DNA Sequencing Kit Technical Manual*, which is incorporated herein by reference. Briefly, 4 µg of plasmid template DNA were alkaline denatured as described for the AMPLITAQ™ reaction (Example 4). The template DNA was then resuspended in 5.5 µl of distilled water, 1.5 µl of reaction buffer and 2.0 µl of primer. The sample was incubated at 65° C. for 5 minutes, then 1 µl of Bst® DNA polymerase, 2 µl of labeling mix and 1 µl of distilled water was added to the reaction. The sample was incubated at 65° C. for 5 minutes. Aliquots (3 µl) were added to each of four tubes containing 6.0 µl of the appropriate termination mixes and incubated at 65° C. for 10 minutes. The reactions were terminated by the addition of 4 µl of stop mix. The reactions were incubated at 70° C. for 2 minutes, then 2.5 µl aliquots were loaded on a 6% polyacrylamide/7M urea sequencing gel, electrophoresed and stained according to the procedure described in Example 1.

Reference is now made to Sample 6 of FIG. 2, which shows the silver-stained sequencing ladder of DNA sequenced by this protocol.

It is understood that the invention is not confined to the particular construction and arrangement herein described, but embraces such modified forms thereof as come within the scope of the claims following the bibliographic citations.

BIBLIOGRAPHY

U.S. Pat. No. 4,804,748 to Barr, et al.
U.S. Pat. No. 4,855,225 to Smith, et al.
U.S. Pat. No. 4,994,372 to Tabor and Richardson.
U.S. Pat. No. 5,047,519 to Prober, et al.
U.S. Pat. No. 5,075,216 to Brow et al.
International Patent Application Publication WO 17611 to Caetano-Anolles, et al.
Bassam, B. J. et al., 1991, *Anal. Biochem.* 196: 80–83.
Beidler, J. L., et al., 1982, *Anal. Biochem.* 126: 374–380.
Boulikas and Hancock, 1981, *J. Biochem. Biophy. Meth.*, 5: 219–228.
Craxton, M., 1991, *Methods* 3: 20–26.
Kobayashi, Y., 1988, *Focus* 1084: 73–74.
Martin et al., 1991, *BioTechniques*, 11: 110–113.
Maxam A. M. and W. Gilbert, 1977, *Proc. Natl. Acad. Sci. USA* 74: 560.
Maxam A. M. and W. Gilbert, 1980, *Meth. Enzymol.* 65: 499.
Sambrook, J., et al., 1989, *Molecular Cloning—A Laboratory Manual* (2nd Edition), Cold Spring Harbor Laboratory Press, New York.
Sanger, F., et al., 1977, *Proc. Natl. Acad. Sci. USA* 74: 5463–5467.
Somerville, L. L. and Wang, K., 1981, *Biochem. Biophys. Res. Comm.* 102: #1 53–58.
Voss, et al., 1992, *Meth. Mol. Cell Biol.*, 3: 30–34.
Watson, J. D., et al., 1987, *Mol. Biol. Gene*, The Benjamin/Cummings Publishing Company, Inc., California, pp. 274–276.
Yudelson, J. et al., 1984, *Biotechniques*, I.

We claim:

1. A high resolution method for determining the nucleotide base sequence of a nucleic acid comprising:
   a. sequencing the nucleic acid by forming a set of fragments of the nucleic acid, wherein the set of fragments includes nucleic acid fragments differing in length by one or more nucleotides;
   b. electrophoretically separating the set of fragments on a gel medium;
   c. exposing the gel medium to a solution containing a sufficient amount of silver nitrate and a reducing agent for a time sufficient to react the set of fragments with the solution;
   d. exposing the gel medium to a developing solution for a time sufficient to visualize the set of fragments; and
   e. determining the sequence of the nucleic acid by viewing the set of reacted fragments.

2. The method of claim 1 wherein the nucleic acid is sequenced according to the enzymatic dideoxy-mediated chain termination method.

3. The method of claim 2 wherein the steps for determining the nucleotide base sequence of the nucleic acid comprise:
   a. hybridizing a primer to a nucleic acid template to be sequenced;
   b. extending the primer under sequencing conditions; and
   c. separating the synthesized fragments according to their size, whereby at least a part of the nucleotide base sequence of the nucleic acid can be determined.

4. The method of claim 3 wherein the primer is an oligonucleotide primer.

5. The method of claim 4 further comprising incorporating a strand terminating nucleotide onto the extended primer under conditions to yield a distinct population of nucleotide fragments beginning on the same 5' nucleotide position for all populations and having a variable terminus at one of the following four nucleotide bases: adenine, cytosine, guanine and thymine.

6. The method of claim 3 wherein the sequencing conditions comprise extending the primer with a DNA polymerase selected from the group consisting of Klenow fragment of *E. coli* DNA polymerase I, reverse transcriptase, SEQUENASE™, SEQUENASE™ Version 2.0, bacteriophage T7 DNA polymerase, and thermal stable DNA polymerases.

7. The method of claim 6 wherein the thermal stable DNA polymerase is selected from the group consisting of *Thermus aquaticus* DNA polymerase, AMPLITAQ™, Sequencing Grade *Thermus aquaticus* DNA polymerase, ΔTaq™ DNA polymerase, Stoffel fragment DNA polymerase, *Thermococcus litoralis* DNA polymerase, *Thermus thermophilus* DNA polymerase, *Bacillus caldotenax* DNA polymerase, *Thermus flavus* DNA polymerase, and *Bacillus stearothermophilus* DNA polymerase.

8. The method of claim 3 wherein the DNA sequencing conditions comprise extending the primer with a thermal stable DNA polymerase under thermocycling conditions.

9. The method of claim 3 wherein the DNA sequencing conditions comprise extending the primer with a DNA polymerase under non-thermocycling conditions.

10. A high resolution method for determining the nucleotide base sequence of DNA comprising:
    a. hybridizing a primer to a DNA template to be sequenced;
    b. extending the primer with a DNA polymerase;
    c. incorporating a strand-terminating nucleotide onto the extended primer under conditions to yield a distinct population of nucleotide fragments beginning on the same 5' nucleotide position for all populations and having a variable terminus at one of the following four nucleotide bases: adenine, cytosine, guanine and thymine; and
    d. separating the synthesized fragments according to their size by denaturing polyacrylamide gel electrophoresis, wherein the population of nucleotide fragments includes DNA fragments differing in length by one or more nucleotides, whereby at least a part of the nucleotide base sequence of the DNA can be determined;
    e. exposing the gel medium to a sufficient amount of silver nitrate and a reducing agent for a time sufficient to react the fragments with the solution;
    f. exposing the gel medium to a developing solution for a time sufficient to visualize the set of fragments; and
    g. determining the sequence of the DNA by viewing the reacted fragments.

11. The method of claim 10 wherein the sequencing conditions comprise extending the primer with a DNA polymerase selected from the group consisting of Klenow fragment of *E. coli* DNA polymerase I, reverse transcriptase, SEQUENASE™, SEQUENASE™ Version 2.0, bacteriophage T7 DNA polymerase, and thermal stable DNA polymerases.

12. The method of claim 10 wherein the DNA polymerase is a thermal-stable DNA polymerase.

13. The method of claim 12 wherein the thermal stable DNA polymerase is selected from the group consisting of *Thermus aquaticus* DNA polymerase, AMPLITAQ™ DNA polymerase, Stoffel fragment DNA polymerase, Sequencing Grade *Thermus aquaticus* DNA polymerase, ΔTaq™ DNA polymerase, *Thermococcus litoralis* DNA polymerase, *Thermus thermophilus* DNA polymerase, *Bacillus caldotenax* DNA polymerase, *Thermus flavus* DNA polymerase, and *Bacillus stearothermophilus* DNA polymerase.

14. The method of claim 10 wherein the DNA template is selected from the group consisting of single-stranded DNA and double-stranded DNA.

15. The method of claim 10 wherein the determination of the DNA sequence further comprises a set of four different sequencing reactions, wherein each sequencing reaction contains a different strand terminating nucleotide which terminates nucleotide synthesis at a specific nucleotide base wherein each reaction yields a distinct population of nucleotide fragments.

16. A silver staining sequencing kit for DNA sequencing comprising:
   a. a container containing a DNA polymerase;
   b. a container containing a DNA sequencing buffer;
   c. a container containing a fix/stop solution;
   d. a container containing sequencing stop solution;
   e. containers containing deoxynucleotide and dideoxynucleotide mixes;
   f. a container containing a silver staining solution comprising silver nitrate and formaldehyde;
   g. a container containing a developer solution; and
   h. instructions for use.

17. A silver staining sequencing kit for DNA sequencing comprising:
   a. a container containing a DNA polymerase;
   b. a container containing a DNA sequencing buffer;
   c. a container containing a fix/stop solution;
   d. a container containing sequencing stop solution;
   e. containers containing deoxynucleotide and dideoxynucleotide mixes;
   f. a container containing a silver staining solution;
   g. a container containing a developer solution comprising sodium carbonate, formaldehyde, and sodium thiosulfate; and
   h. instructions for use.

18. The method according to claim 1, wherein the reducing agent is formaldehyde.

19. The method according to claim 1, wherein the developing solution comprises carbonate, formaldehyde, and thiosulfate pentahydrate.

20. The method according to claim 10, wherein the reducing agent is formaldehyde.

21. The method according to claim 10, wherein the developing solution comprises carbonate, formaldehyde, and thiosulfate pentahydrate.

22. The kit of claim 16 further comprising sequencing primers and DNA templates for use in a control reaction.

23. The kit of claim 22 wherein the primer is pUC/M13 forward 24 mer and the DNA template is pGEM®-3Zf(+).

24. The kit of claim 17 further comprising sequencing primers and DNA templates for use in a control reaction.

25. The kit of claim 24 wherein the primer is pUC/M13 forward 24 mer and the DNA template is pGEM®-3Zf(+).

* * * * *